United States Patent
Hsieh et al.

(10) Patent No.: US 11,342,078 B2
(45) Date of Patent: May 24, 2022

(54) BLOOD VESSEL STATUS EVALUATION METHOD AND BLOOD VESSEL STATUS EVALUATION DEVICE

(71) Applicants: Acer Incorporated, New Taipei (TW); Far Eastern Memorial Hospital, New Taipei (TW)

(72) Inventors: Cheng-Tien Hsieh, New Taipei (TW); Ai-Hsien Li, New Taipei (TW)

(73) Assignees: ACER INCORPORATED, New Taipei (TW); FAR EASTERN MEMORIAL HOSPITAL, New Taipei (TW)

(*) Notice: Subject to any disclaimer, the term of this patent is extended or adjusted under 35 U.S.C. 154(b) by 69 days.

(21) Appl. No.: 16/666,427

(22) Filed: Oct. 29, 2019

(65) Prior Publication Data

US 2021/0012901 A1    Jan. 14, 2021

(30) Foreign Application Priority Data

Jul. 11, 2019 (TW) ................... 108124403

(51) Int. Cl.
*G16H 50/30* (2018.01)
*G16H 50/20* (2018.01)
(Continued)

(52) U.S. Cl.
CPC ........... *G16H 50/30* (2018.01); *G06T 7/0012* (2013.01); *G16H 30/40* (2018.01); *G16H 50/20* (2018.01);
(Continued)

(58) Field of Classification Search
CPC ........ G16H 50/30; G16H 50/20; G16H 30/40; G16H 50/50; G06T 7/0012;
(Continued)

(56) References Cited

U.S. PATENT DOCUMENTS 7,853,061 B2 * 12/2010 Gorges .................. G06T 15/503
382/128
2006/0050966 A1    3/2006 Nishimura et al.
(Continued)

FOREIGN PATENT DOCUMENTS

CN    104867147        8/2015
CN    108830155 A  * 11/2018
(Continued)

OTHER PUBLICATIONS

Translation of CN-109658407-A (Year: 2019).*
Machine translation of CN-108830155-A (Year: 2018).*

*Primary Examiner* — Vu Le
*Assistant Examiner* — Courtney Joan Nelson
(74) *Attorney, Agent, or Firm* — JCIPRNET

(57) ABSTRACT

A blood vessel status evaluation method and a blood vessel status evaluation device are provided. The method includes: obtaining at least one angiography image corresponding to a target user; analyzing the angiography image by a first deep learning model to select a target image from the angiography image; analyzing the target image by at least one second deep learning model to determine a blood vessel type of the target user and divide a target blood vessel pattern in the target image into a plurality of scoring segments; and analyzing an output of the second deep learning model by a third deep learning model to obtain a blood vessel status of the target user.

12 Claims, 8 Drawing Sheets

(51) Int. Cl.
*G16H 30/40* (2018.01)
*G06T 7/00* (2017.01)

(52) U.S. Cl.
CPC ............... *G06T 2207/20081* (2013.01); *G06T 2207/30101* (2013.01)

(58) Field of Classification Search
CPC . G06T 2207/20081; G06T 2207/30101; G06T 7/0002; G06T 7/00; G06T 7/10; G06T 2207/20; G06T 2207/30004; G06T 2207/30
See application file for complete search history.

(56) References Cited

U.S. PATENT DOCUMENTS

| | | | |
|---|---|---|---|
| 2016/0157802 A1* | 6/2016 | Anderson | A61B 5/0215 600/427 |
| 2019/0125193 A1* | 5/2019 | Saito | G06K 9/6271 |

FOREIGN PATENT DOCUMENTS

| | | | | |
|---|---|---|---|---|
| CN | 109658407 | | 4/2019 | |
| CN | 109658407 A | * | 4/2019 | |
| TW | 201903708 | | 1/2019 | |
| WO | WO-2008016652 A2 | * | 2/2008 | ............. A61B 6/032 |

* cited by examiner

| Scoring segment | Focus 0 | ................. | Focus 19 |
|---|---|---|---|
| 1 | T/F | ................. | T/F |
| 2 | T/F | ................. | T/F |
| ⋮ | ⋮ | ................. | ⋮ |
| 15 | T/F | ................. | T/F |

FIG. 7

BLOOD VESSEL STATUS EVALUATION METHOD AND BLOOD VESSEL STATUS EVALUATION DEVICE

CROSS-REFERENCE TO RELATED APPLICATION

This application claims the priority benefit of Taiwan application serial no. 108124403, filed on Jul. 11, 2019. The entirety of the above-mentioned patent application is hereby incorporated by reference herein and made a part of this specification.

BACKGROUND

Technical Field

The invention relates to a physiological status evaluation technology based on deep learning, in particular, to a blood vessel status evaluation method and a blood vessel status evaluation device.

Description of Related Art

Along with change of the dietary habit of modern people, cardiovascular disease has been found in more and more young people. Because cardiovascular occlusion may cause myocardial infarction while acute myocardial infarction often leads to loss of life, keeping the cardiovascular non-occluded is urgent. Generally speaking, if cardiovascular occlusion occurs, apart from taking medicine, the condition may also be controlled by adopting a balloon expansion or a stent placement in the cardiac catheter surgery of the cardiology department. In serious cases, the coronary artery bypass surgery of the cardiac surgery department may also be selected. Moreover, a SYNTAX scoring is an evaluation method for the stent placement or the bypass surgery that calculates the occlusion degree of heart blood vessels by angiography. However, the SYNTAX scoring mechanism is so extremely complicated that a doctor or a medical technologist needs to research and judge the blood vessel status according to the angiography image and execute a complicated scoring procedure.

SUMMARY

The invention provides a blood vessel status evaluation method and a blood vessel status evaluation device, which can effectively increase the blood vessel status evaluation efficiency.

The embodiment of the invention provides a blood vessel status evaluation method, including: obtaining at least one angiography image corresponding to a target patient; analyzing the at least one angiography image by a first deep learning model to select a target image from the at least one angiography image; analyzing the target image by at least one second deep learning model to determine a blood vessel type of the target patient and divide a target blood vessel pattern in the target image to a plurality of scoring segments; and analyzing an output of the second deep learning model by a third deep learning model to obtain a blood vessel status of the target patient.

The embodiment of the invention also provides a blood vessel status evaluation device, including a storage device and a processor. The storage device is used for storing at least one angiography image corresponding to a target patient. The processor is coupled to the storage device. The processor is used for analyzing the at least one angiography image by a first deep learning model to select a target image from the at least one angiography image. The processor is further used for analyzing the target image by at least one second deep learning model to determine a blood vessel type of the target patient and divide a target blood vessel pattern in the target image into a plurality of scoring segments. The processor is further used for analyzing an output of the at least one second deep learning model by a third deep learning model to obtain a blood vessel status of the target patient.

Based on the foregoing, after the at least one angiography image corresponding to the target patient is obtained, the angiography image is analyzed by the first deep learning model, so that the target image may be selected. Then the target image is analyzed by the second deep learning model, so that the blood vessel type of the target patient may be determined and the target blood vessel pattern in the target image may be divided into the scoring segments. Moreover, an output of the second deep learning model is analyzed by the third deep learning model, so that the blood vessel status of the target patient may obtained. Accordingly, the blood vessel status evaluation efficiency may be effectively increased In order to make the aforementioned and other objectives and advantages of the invention comprehensible, embodiments accompanied with figures are described in detail below.

BRIEF DESCRIPTION OF THE DRAWINGS

FIG. 7 is a schematic diagram of evaluation information drawn according to an embodiment of the invention.

DESCRIPTION OF THE EMBODIMENTS

Figure 1:
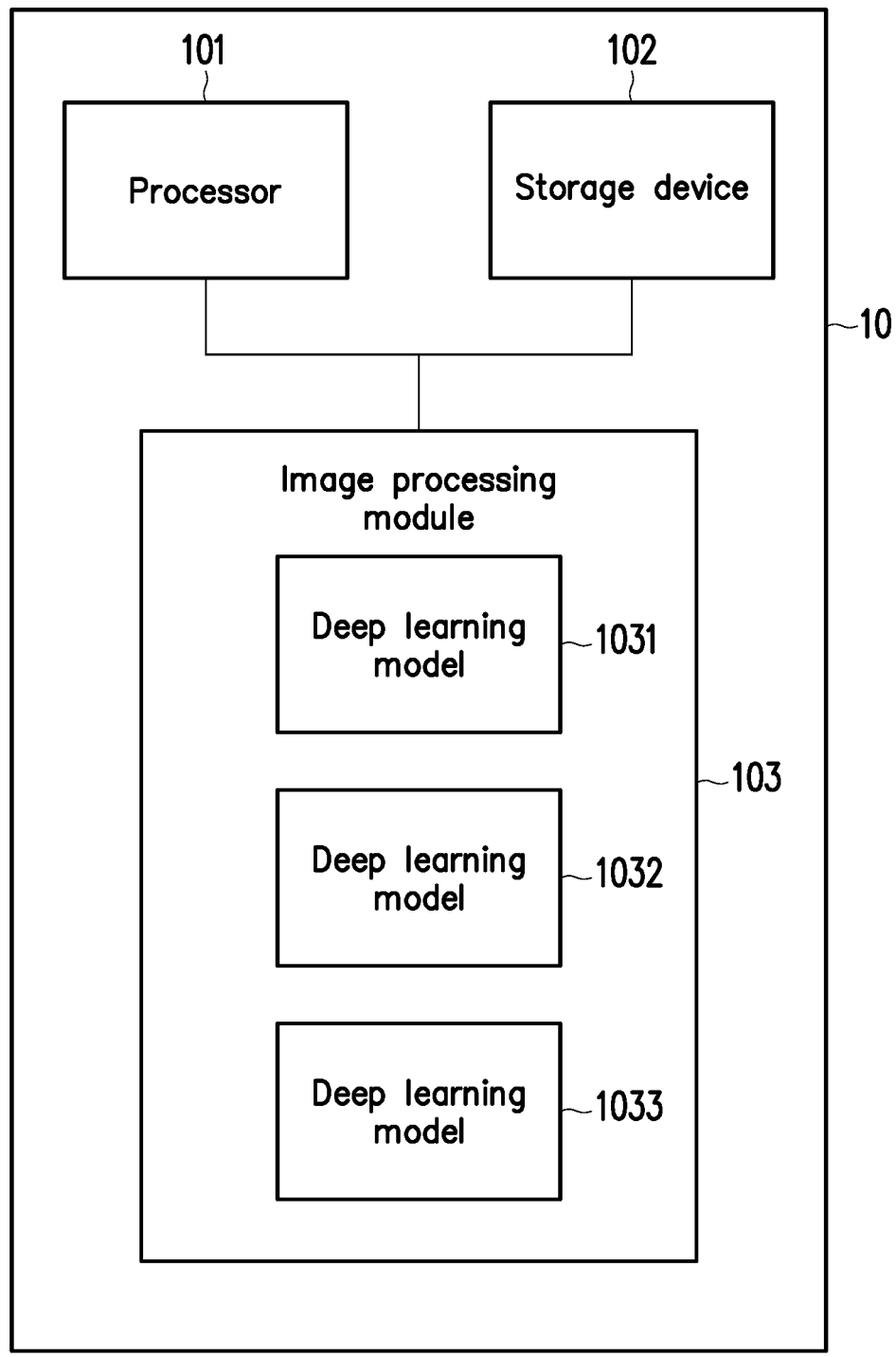
FIG. 1 is a schematic diagram of a blood vessel status evaluation device drawn according to an embodiment of the invention.

FIG. 1 is a schematic diagram of a blood vessel status evaluation device drawn according to an embodiment of the invention. Referring to FIG. 1, in an embodiment, a device (also named as a blood vessel status evaluation device) 10 may be an electronic device or a computer device with an image analysis and operation function. In another embodiment, the device 10 may also be an inspection equipment for cardiovascular status or an image capture equipment used for angiocardiography. The device 10 may also be used for automatically analyzing an angiography image of a certain patient (also named as a target patient) and automatically generating evaluation information to reflect a blood vessel status of a target patient. In an embodiment, a developing agent may be injected into the heart blood vessel (for example, the coronary artery) of the target patient and used to photograph the heart blood vessel of the target patient, so as to obtain the angiography image.

The device 10 includes a processor 101, a storage device 102 and an image processing module 103. The processor 101 is coupled to the storage device 102 and the image processing module 103. The processor 101 may be a central processing unit (CPU), a graphics processing unit (GPU), or other programmable microprocessors for general purposes or special purposes, a digital signal processor (DSP), a programmable controller, application specific integrated circuits (ASIC), a programmable logic device (PLD) or other similar devices or combination of these devices. The processor 101 may be in charge of the overall or partial operation of the device 10.

The storage device 102 is used for storing an image (namely, the angiography image) and other data. The storage device 102 may include a volatile storage medium and a non-volatile storage medium. The volatile storage medium may include a random access memory (RAM), while the non-volatile storage medium may include a read-only memory (ROM), a solid state disk (SSD) or a traditional hard disk (HDD) and the like.

The image processing module 103 is used for executing image recognition on the image stored by the storage device 102 so as to identify patterns in the image by machine vision. The image processing module 103 may be implemented by a software module, a firmware module or a hardware circuit. For example, in an embodiment, the image processing module 103 may include at least one graphics processing unit (GPU) or a similar processing wafer to execute the image recognition. Alternatively, in an embodiment, the image processing module 103 is a program code that may be loaded into the storage device 102 and executed by the processor 101. In an embodiment, the image processing module 103 may also be implemented in the processor 101.

It should be noted that, the image processing module 103 includes an artificial intelligent architecture of machine learning and/or deep learning and the like that can continuously improve the image recognition performance thereof through trainings. For example, the image processing module 103 includes a deep learning model (also named as a first deep learning model) 1031, a deep learning model (also named as a second deep learning model) 1032 and a deep learning model (also named as a third deep learning model) 1033. All deep learning models in the image processing module 103 may be independent from one another or may communicate with one another. Moreover, in an embodiment, the device 10 may also include input/output devices of a mouse, a keyboard, a display, a microphone, a loudspeaker or a network interface card and the like, and the type of the input/output devices is not limited herein.

Figure 2:
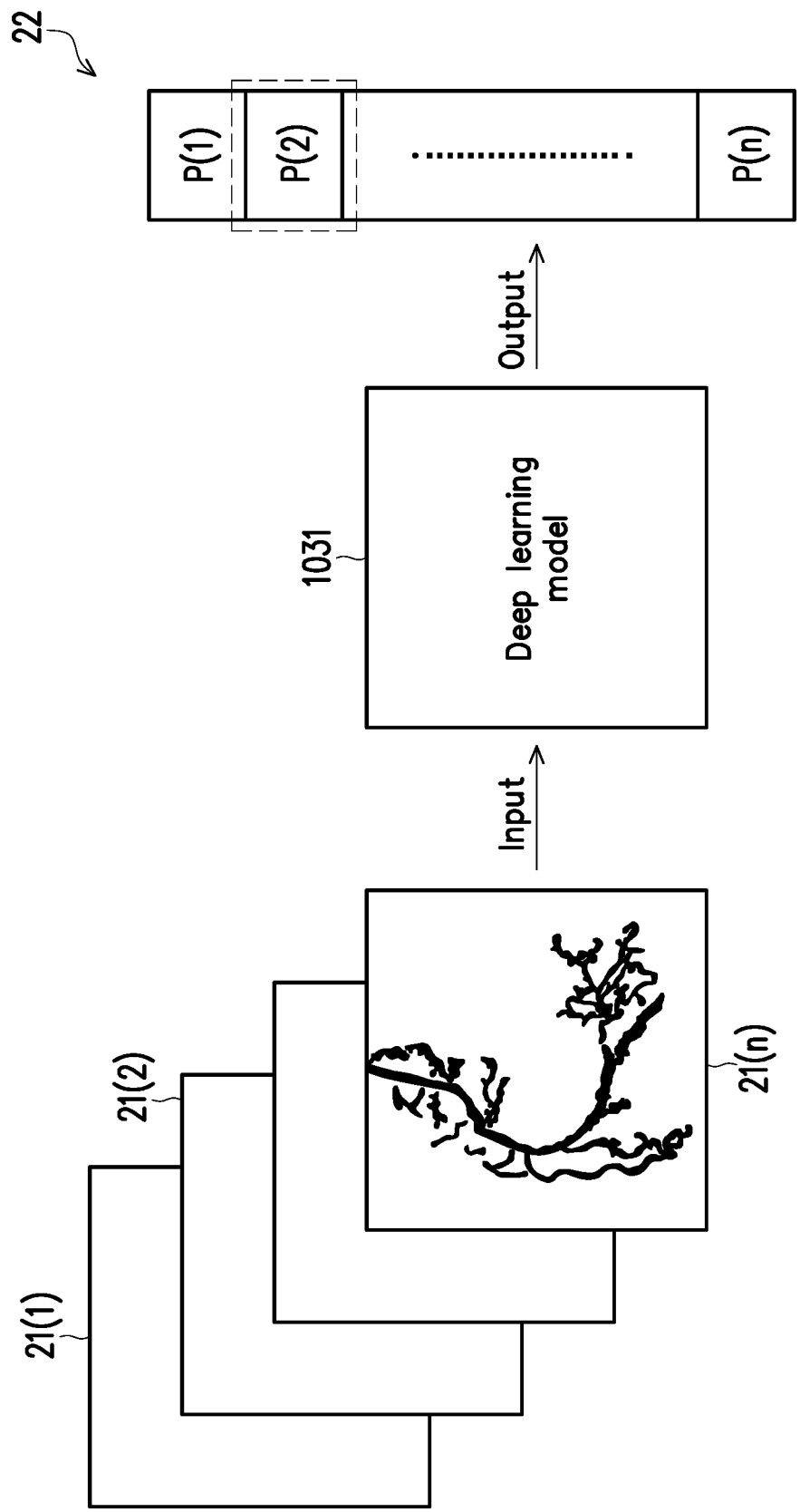
FIG. 2 is a schematic diagram of analyzing an image by a first deep learning model drawn according to an embodiment of the invention.

FIG. 2 is a schematic diagram of analyzing an image by a first deep learning model drawn according to an embodiment of the invention. Referring to FIG. 1 and FIG. 2, the storage device 102 may store a plurality of images 21(1)-21(n). The images 21(1)-21(n) may belong to one or more video files. The images 21(1)-21(n) are all angiography images corresponding to the same target patient. The processor 101 may select one or more images (also named as a target image) from the images 21(1)-21(n) by the deep learning mode 1031. For example, the deep learning model 1031 may include learning models related to a time series, such as a recurrent neural network (RNN) model and/or a long short term memory (LSTM).

According to analysis results of the images 21(1)-21(n), the deep learning model 1031 may output a sequence 22 containing n probability values P(1)-P(n). The probability values P(1)-P(n) respectively correspond to the images 21(1)-21(n). For example, the probability value P(i) corresponds to the image 21(i). i is between 1 and n. The probability value P(i) is between 0 and 1. The probability value P(i) may represent the probability that the image 21(i) participates in a subsequent operation. The processor 101 may compare the probability values P(1)-P(n) respectively with a preset value. If the probability value P(i) is higher than the preset value, the processor 101 may determine the image 21(i) corresponding to the probability value P(i) as the target image.

After the target image is selected, the processor 101 may analyze the target image by the deep learning model 1032 to determine the blood vessel type of the target patient and divide the blood vessel pattern (also named as the target blood vessel pattern) in the target image into a plurality of scoring segments. For example, division of the scoring segments conforms to SYNTAX or a similar standard. For example, the deep learning model 1032 may include neural network models related to encoding and decoding such as a convolutional neural network (CNN) model, a full convolutional network (FCN), a region-based CNN and/or U-Net model and the like.

Figure 3:
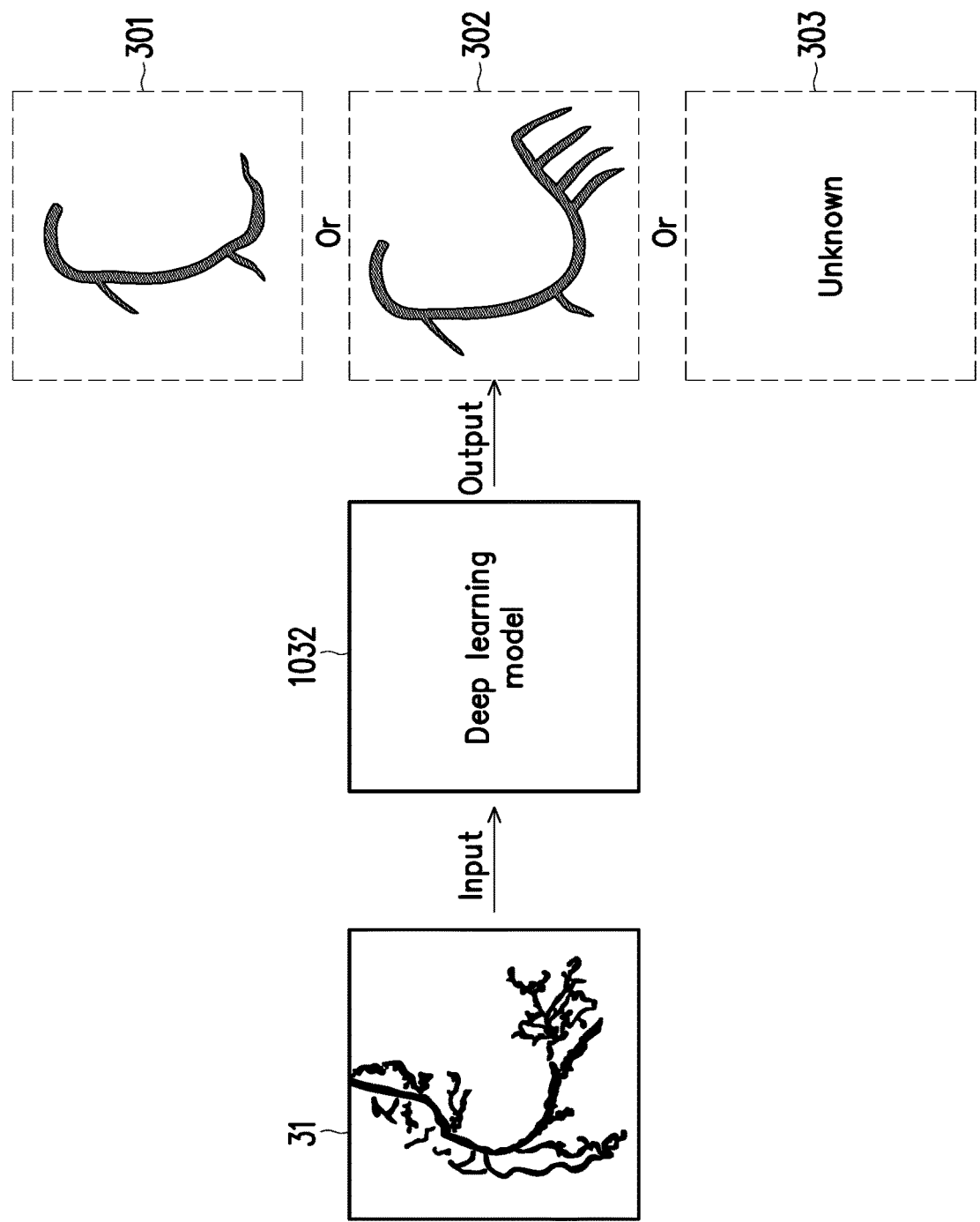
FIG. 3 is a schematic diagram of analyzing the image by a second deep learning model drawn according to an embodiment of the invention.

FIG. 3 is a schematic diagram of analyzing the image by a second deep learning model drawn according to an embodiment of the invention. Referring to FIG. 1 and FIG. 3, it is assumed that an image 31 is the target image. The processor 101 may analyze the image 31 by the deep learning model 1032 to determine the blood vessel type of the target patient. On the other hand, the processor 101 may divide the blood vessel pattern (also named as the target blood vessel pattern) in the image 31 into a plurality of scoring segments by the deep learning model 1032. It should be noted that, the operation of determining the blood vessel type of the target patient and the operation of dividing the target blood vessel pattern in the target image into the scoring segments are executed by one or more sub-deep learning models in the deep learning model 1032.

According to the analysis result of the image 31, the deep learning model 1032 may determine that the blood vessel type of the target patient is one of left dominance 301 and right dominance 302. For example, the left dominance 301 and the right dominance 302 may reflect two different types of the right coronary artery. Moreover, if the analysis result of the image 31 does not conform to any one of the left dominance 301 and the right dominance 302, the deep learning model 1032 may also determine that the blood vessel type of the target patient is unknown 303. If the blood vessel type of the target patient is unknown 303, the processor 101 may re-execute the operation of FIG. 2 to select a new target image. Then, the operation of FIG. 3 may be executed on the new target image to re-identify the blood vessel type of the target patient as the left dominance 301 or the right dominance 302.

In an embodiment, a certain sub-deep learning model in the deep learning model 1032 may be used for inspecting the reasonability of the target image selected by the deep learning model 1031. For example, if the deep learning model 1032 determines that the blood vessel type of the target patient is unknown 303 of FIG. 3 according to the currently selected target image, the sub-deep learning model may determine the reasonability of the currently selected target image as negative. If the reasonability of the currently selected target image is insufficient, the processor 101 may re-select another image as the target image by the deep learning model 1031. The deep learning model 1032 may determine the reasonability of the new target image again. Alternatively, if the deep learning model 1032 determines the blood vessel type of the target patient as the left dominance 301 or the right dominance 302 of FIG. 3 according to the currently selected target image, the sub-deep learning model may determine the reasonability of the currently selected target image as positive and the processor 101 may execute a subsequent procedure according to a determination result.

Figure 4:
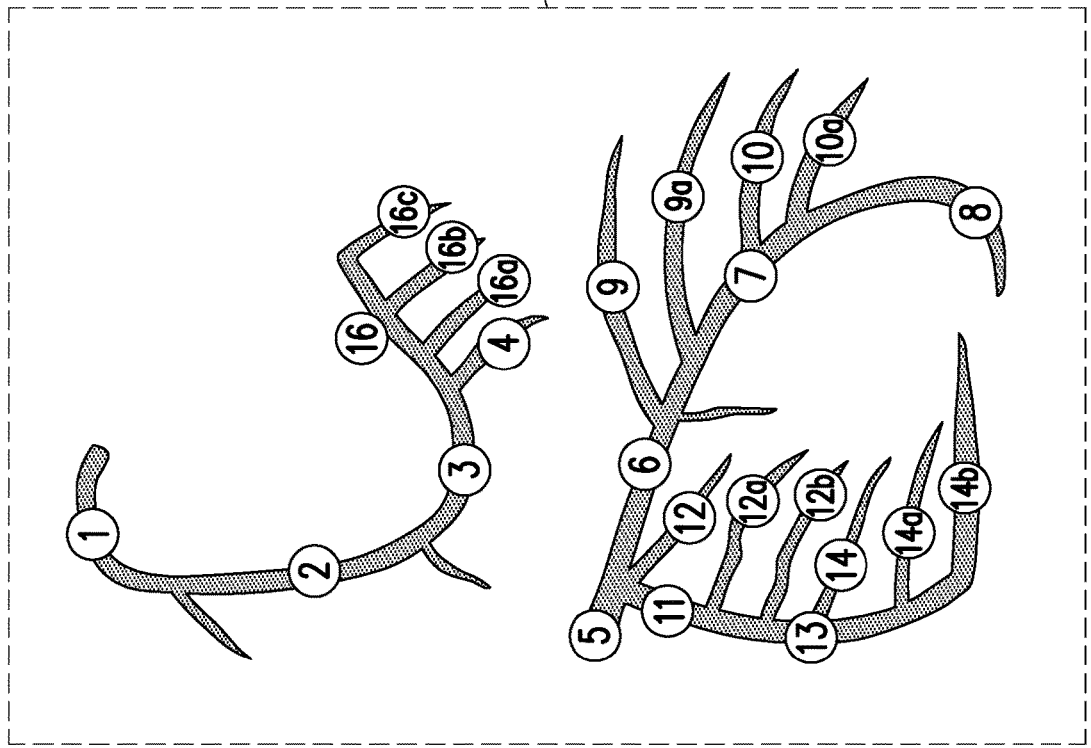
FIG. 4 is a schematic diagram of scoring rules and corresponding scoring segments drawn according to an embodiment of the invention.
Figure 4:
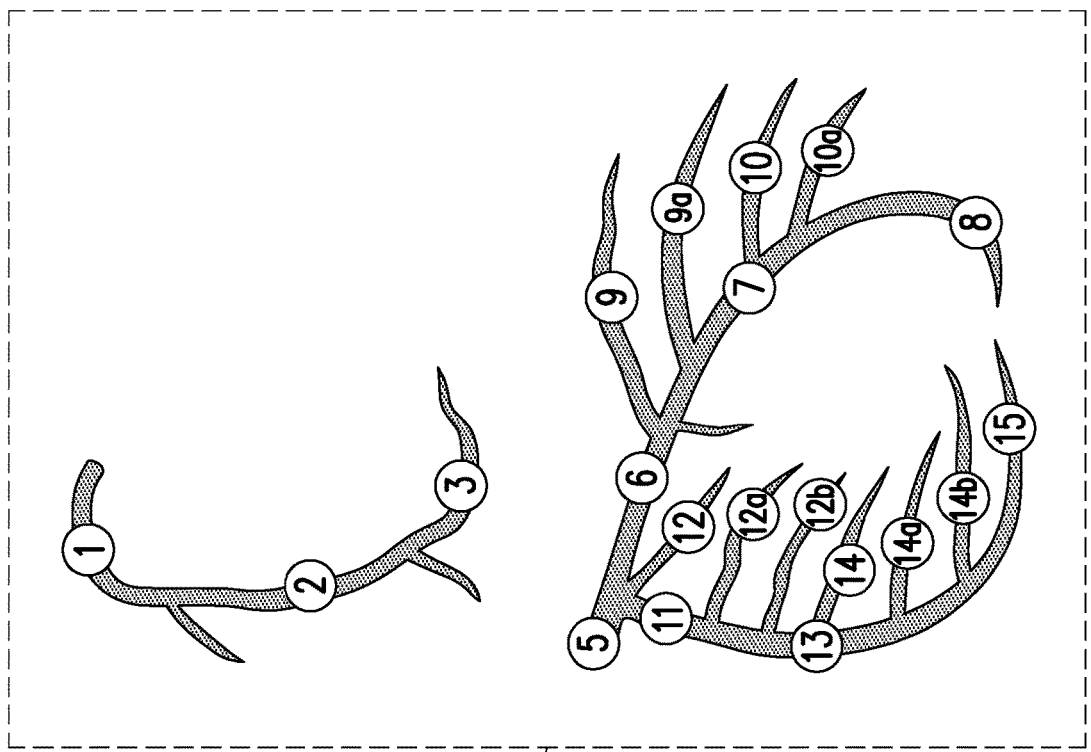

FIG. 4 is a schematic diagram of scoring rules and corresponding scoring segments drawn according to an embodiment of the invention. Referring to FIG. 3 and FIG. 4, scoring rules 41 and 42 respectively correspond to the left dominance 301 and the right dominance 302. If the blood vessel type of the target patient is the left dominance 301, scoring is performed on the blood vessel occlusion status in the scoring segments marked with numerical values 1-15 based on the scoring rule 41. Alternatively, if the blood vessel type of the target patient is the right dominance 302, scoring is performed on the blood vessel occlusion status in the scoring segments marked with numerical values 1-15, 16 and 16a-16c based on the scoring rule 42. Therefore, according to the analysis result of the image 31, the deep learning model 1032 divides the target blood vessel pattern in the image 31 into a plurality of scoring segments according to one of the scoring rules 41 and 42.

Figure 5:
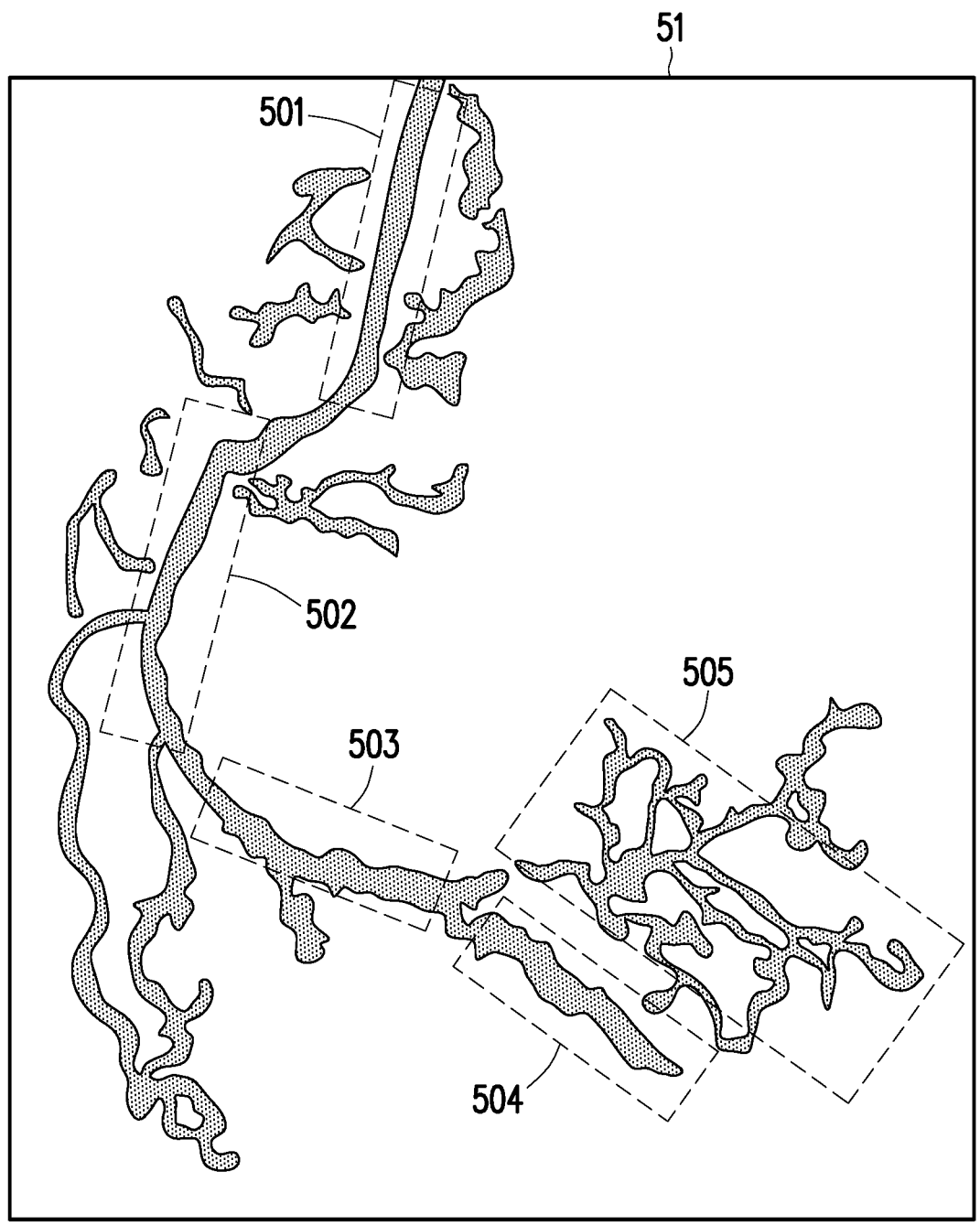
FIG. 5 is a schematic diagram of forming the scoring segments through division drawn according to an embodiment of the invention.

FIG. 5 is a schematic diagram of forming the scoring segments through division drawn according to an embodiment of the invention. Referring to FIG. 3 to FIG. 5, in an embodiment, it is assumed that the blood vessel type of the target patient is the right dominance 302. The deep learning model 1032 may divide the blood vessel pattern (that is, the target blood vessel pattern) in an image 51 into scoring segments 501-505 according to the right dominance 302. The scoring segment 501 corresponds to a segment 1 indicated by the scoring rule 42; the scoring segment 502 corresponds to a segment 2 indicated by the scoring rule 42; the scoring segment 503 corresponds to a segment 3 indicated by the scoring rule 42; the scoring segment 504 corresponds to a segment 4 indicated by the scoring rule 42; and the scoring segment 505 corresponds to the segments 16 and 16a-16c indicated by the scoring rule 42. It should be noted that, in another embodiment, if the blood vessel type of the target patient is the left dominance 301, the deep learning model 1032 may also divide the target blood vessel pattern in the target image into a plurality of corresponding scoring segments based on the segments 1-15 indicated by the scoring rule 41.

Referring back to FIG. 1, after the target blood vessel pattern in the target image is divided into the scoring segments, the processor 101 may analyze an output of the deep learning model 1032 by the deep learning model 1033 to obtain the blood vessel status of the target patient. For example, the deep learning model 1033 may include a CNN model (for example, VGGNet or ResNet) or other suitable learning models.

Figure 6:
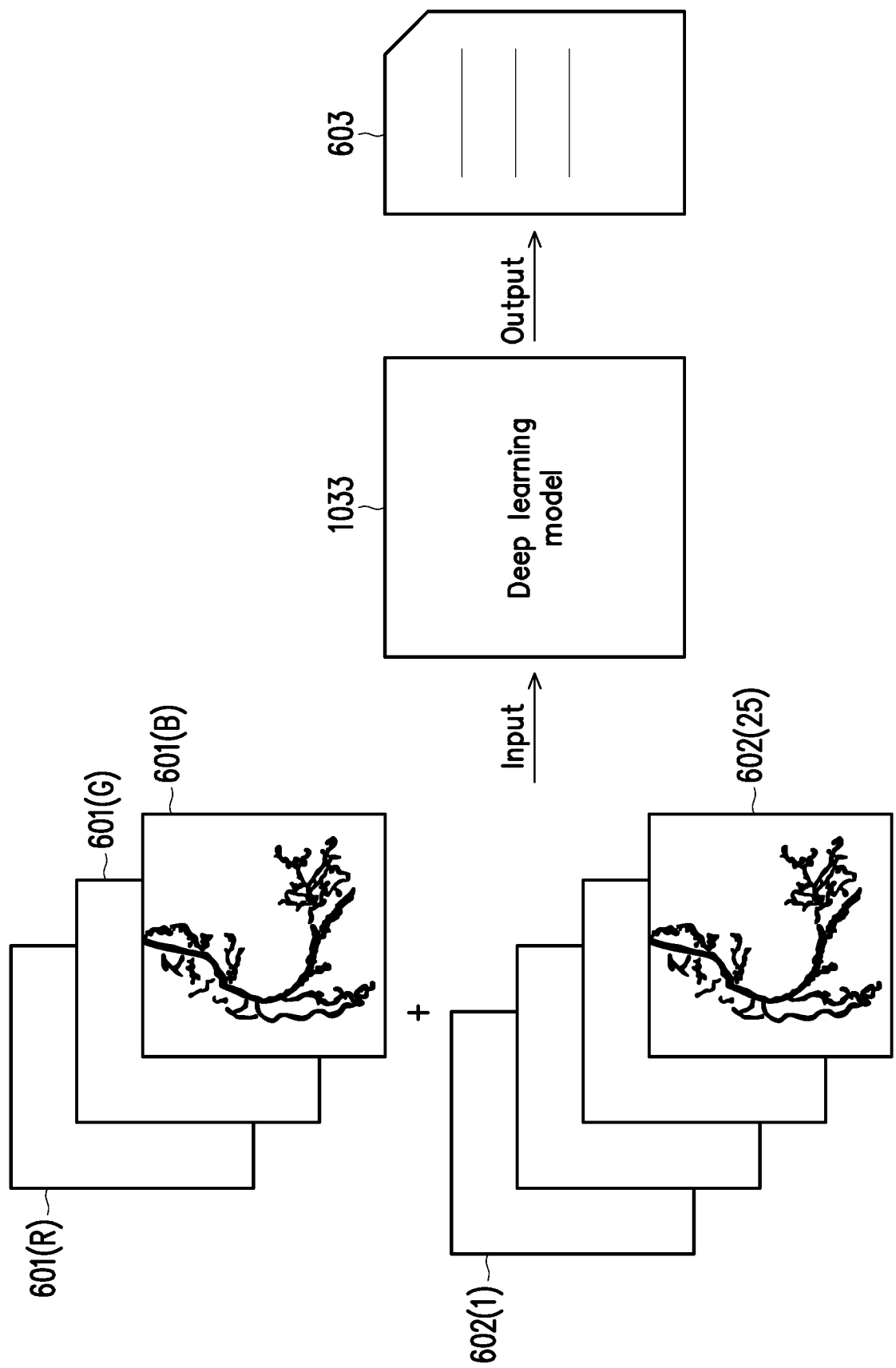
FIG. 6 is a schematic diagram of analyzing the image by a third deep learning model drawn according to an embodiment of the invention.

FIG. 6 is a schematic diagram of analyzing the image by a third deep learning model drawn according to an embodiment of the invention. Referring to FIG. 6, in an embodiment, the deep learning model 1033 may obtain a plurality of monochrome images 601(R), 601(G) and 601(B) corresponding to the target image. For example, the monochrome images 601(R), 601(G) and 601(B) may be obtained by executing color filtering on the target image, so as to present the target image with single colors (for example, red, green and blue) respectively. In certain circumstances, accuracy for analyzing the monochrome images is higher than the accuracy for analyzing color images.

The deep learning model 1033 may also obtain a plurality of shielded images 602(1)-602($p$) corresponding to the plurality of divided scoring segments. For example, the processor 101 of FIG. 1 may generate a plurality of corresponding shielded images 602(1)-602($p$) according to p scoring segments divided by the deep learning model 1032. p may be between numerical values 2 and 25 (corresponding to the SYNTAX scoring standard). Taking FIG. 5 as an example, the shielded image 602(1) may be generated according to the divided scoring segment 501 and used for analyzing the blood vessel status in the scoring segment 501, the shielded image 602(2) may be generated according to the divided scoring segment 502 and used for analyzing the blood vessel status in the scoring segment 502, and the rest may be deduced by analogy. In an embodiment, the sum of the shielded images 602(1)-602($p$) (i.e., the value p) may be different according to whether the blood vessel type of the target patient is the left dominance or the right dominance.

The deep learning model 1033 may analyze the monochrome images 601(R), 601(G), 601(B) and the shielded images 602(1)-602($p$) and generate evaluation information 603. The evaluation information 603 may reflect the blood vessel status of the patient. For example, the evaluation information 603 may reflect whether a blood vessel in a certain scoring segment has focuses like total occlusion, trifurcation lesion, bifurcation lesion, aorto-ostial lesion, severe tortuosity or heavy calcification and the like. These focuses, for example, are defined in the SYNTAX scoring standard.

FIG. 7 is a schematic diagram of evaluation information drawn according to an embodiment of the invention. Referring to FIG. 7, evaluation information 71 may be stored in the storage device 102 of FIG. 1 and may be output (for example, being presented on a display) by an input/output interface.

In the present embodiment, the evaluation information 71 may record whether a blood vessel in the scoring segments 1-15 has any focus of focuses 0-19. If the analysis result reflects that the blood vessel in a certain scoring segment (for example, the scoring segment 1) has a certain focus (for example, the focus 0), an intersection field between the scoring segment and the focus (for example, the scoring segment 1 and the focus 0) may be recorded as T. If the analysis result reflects that the blood vessel in a certain scoring segment (for example, the scoring segment 2) has a certain focus (for example, the focus 19), an intersection field between the scoring segment and the focus (for example, the scoring segment 2 and the focus 19) may be recorded as F. Therefore, the evaluation information 71 may clearly reflect the blood vessel status of the target patient. For example, the evaluation information 71 may record a scoring result corresponding to the blood vessel status of one or more scoring segments.

It should be noted that, in an embodiment, the evaluation information 71 may also record relevance information between at least one scoring segment and at least one focus in other forms. Moreover, in another embodiment, the evaluation information 71 may also record more information used for describing the blood vessel status of the target patient, such as the probability that a certain focus occurs in a certain scoring segment. The invention is not limited in this regard.

In an embodiment, the input images (for example, the images 21(1)-21(*n*) of FIG. 2) may contain images from different camera angles. After the images are analyzed by a plurality of deep learning models (for example, the learning models 1031-1033 of FIG. 1), a plurality of scoring results generated by analyzing the images from difference camera angles may be obtained, and these scoring results may be recorded in the evaluation information 71. If different scoring results corresponding to the same scoring segment (also named as the target scoring segment) are generated by analyzing the images of different camera angles, only part of the scoring results may be adopted eventually to describe the blood vessel status of the target scoring segment. For example, a maximum value (that is, the highest score) corresponding to the scoring segment in all the scoring results may be adopted as the final scoring result, so as to describe the blood vessel status of the target scoring segment by the final scoring result.

Figure 8:
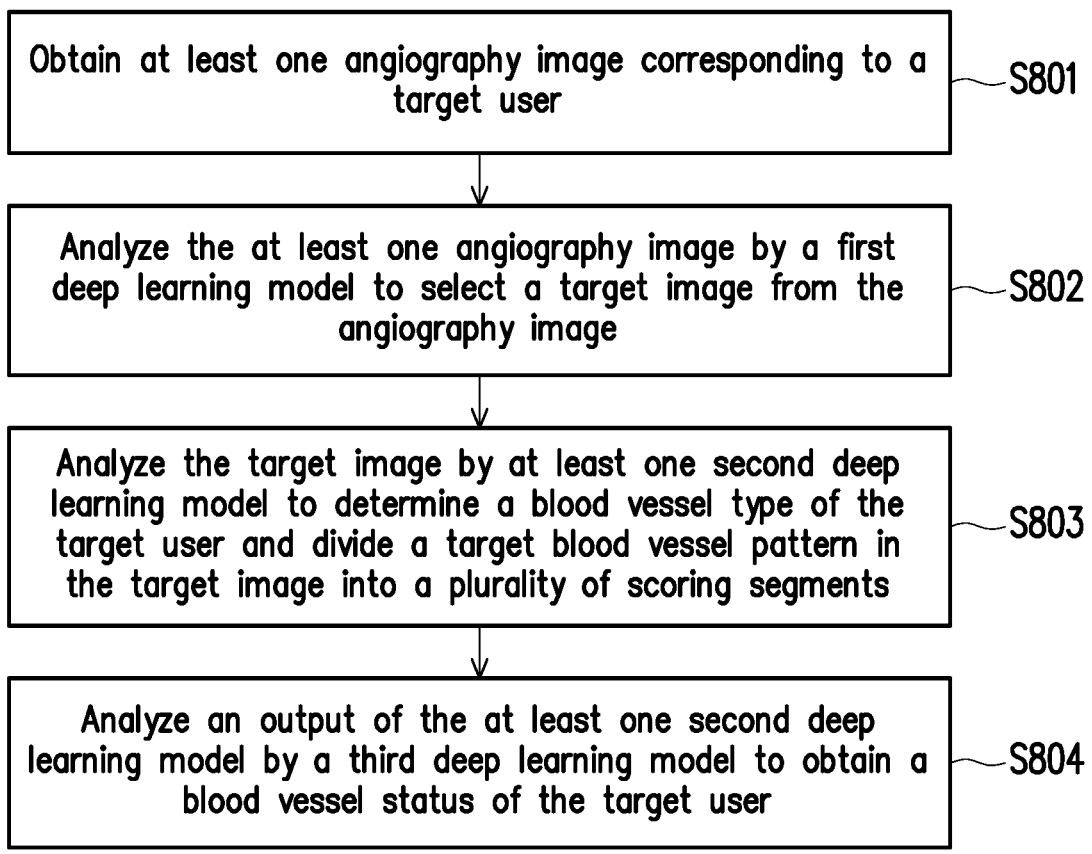
FIG. 8 is a flow diagram of a blood vessel status evaluation method drawn according to an embodiment of the invention.

FIG. 8 is a flow diagram of a blood vessel status evaluation method drawn according to an embodiment of the invention. Referring to FIG. 8, in step S801, at least one angiography image corresponding to a target patient is obtained. In step S802, the angiography image is analyzed by a first deep learning model to select a target image from the angiography image. In step S803, the target image is analyzed by a second deep learning model to determine a blood vessel type of the target patient and divide a target blood vessel pattern in the target image to a plurality of scoring segments. In step S804, an output of the second deep learning model is analyzed by a third deep learning model to obtain a blood vessel status of the target patient.

However, each step in FIG. 8 has already been described in details as above, and will not be further described herein. It is worth noting that, each step in FIG. 8 is taken as a plurality of program codes or circuits, which is not limited in the invention. Moreover, the method of FIG. 8 may be used in match with the foregoing examples and embodiments, or may be independently used, which is not limited in the invention.

In summary, after the at least one angiography image corresponding to the target patient is obtained, the angiography image is analyzed by the first deep learning model, so that the target image may be selected. Then the target image is analyzed by the second deep learning model, so that the blood vessel type of the target patient may be determined and the target blood vessel pattern in the target image may be divided into the scoring segments. Moreover, an output of the second deep learning model is analyzed by the third deep learning model, so that the blood vessel status of the target patient may be obtained. Accordingly, the blood vessel status evaluation efficiency may be effectively increased.

Although the invention is described with reference to the above embodiments, the embodiments are not intended to limit the invention. A person of ordinary skill in the art may make variations and modifications without departing from the spirit and scope of the invention. Therefore, the protection scope of the invention should be subject to the appended claims.

What is claimed is:

1. A blood vessel status evaluation method, comprising:
  obtaining at least one angiography image corresponding to a target patient;
  analyzing the at least one angiography image by a first deep learning model to select a target image from the at least one angiography image;
  analyzing the target image by at least one second deep learning model to determine a blood vessel type of the target patient and divide a target blood vessel pattern in the target image into a plurality of scoring segments; and
  analyzing an output of the at least one second deep learning model by a third deep learning model to obtain a blood vessel status of the target patient,
  wherein the step of analyzing the output of the at least one second deep learning model by the third deep learning model to obtain the blood vessel status of the target patient comprises:
    obtaining a plurality of first type images corresponding to the target image, wherein each of the first type images presents the target image with one single color;
    obtaining a plurality of second type images according to the scoring segments, wherein each of the second type images is used for analyzing a blood vessel status in one of the scoring segments; and
    analyzing the first type images and the second type images to obtain the blood vessel status of the target patient.

2. The blood vessel status evaluation method according to claim 1, wherein the step of analyzing the at least one angiography image by the first deep learning model to select the target image from the at least one angiography image comprises:
  determining a probability value corresponding to a first image in the at least one angiography image by the first deep learning model; and
  if the probability value is higher than a preset value, determining the first image as the target image.

3. The blood vessel status evaluation method according to claim 1, wherein the blood vessel type of the target patient comprises one of left dominance and right dominance.

4. The blood vessel status evaluation method according to claim 1, wherein division of the plurality of scoring segments conforms to a SYNTAX scoring standard.

5. The blood vessel status evaluation method according to claim 1, wherein the blood vessel type of the target patient comprises a first type and a second type, and a distribution of the scoring segments being divided from the target blood vessel pattern in the target image in response to the blood vessel type of the target patient being determined as the first type is different from a distribution of the scoring segments being divided from the target blood vessel pattern in the target image in response to the blood vessel type of the target patient being determined as the second type.

6. The blood vessel status evaluation method according to claim 1, wherein the at least one angiography image comprises a plurality of images from different camera angles, and the step of analyzing the output of the at least one second deep learning model by the third deep learning model to obtain the blood vessel status of the target patient comprises:
  generating a plurality of scoring results corresponding to a target scoring segment; and
  taking a maximum value corresponding to the target scoring segment in the plurality of scoring results as a final scoring result to describe a blood vessel status of the target scoring segment.

7. A blood vessel status evaluation device, comprising:
  a storage device, used for storing at least one angiography image corresponding to a target patient; and
  a processor, coupled to the storage device,
  wherein the processor is used for analyzing the at least one angiography image by a first deep learning model to select a target image from the at least one angiography image, the processor is further used for analyzing the target image by at least one second deep learning model to determine a blood vessel type of the target patient and divide a target blood vessel pattern into the target image to a plurality of scoring segments, and the processor is further used for analyzing an output of the at least one second deep learning model by a third deep learning model to obtain a blood vessel status of the target patient, wherein the operation of analyzing the output of the at least one second deep learning model by the third deep learning model to obtain the blood vessel status of the target patient comprises:

obtaining a plurality of first type images corresponding to the target image, wherein each of the first type images presents the target image with one single color;

obtaining a plurality of second type images according to the scoring segments, wherein each of the second type images is used for analyzing a blood vessel status in one of the scoring segments; and analyzing the first type images and the second type images to obtain the blood vessel status of the target patient.

8. The blood vessel status evaluation device according to claim 7, wherein the operation that the processor analyzes the at least one angiography image by the first deep learning model to select the target image from the at least one angiography image comprises:

determining a probability value corresponding to a first image in the at least one angiography image by the first deep learning model; and if the probability value is higher than a preset value, determining the first image as the target image.

9. The blood vessel status evaluation device according to claim 7, wherein the blood vessel type of the target patient comprises one of left dominance and right dominance.

10. The blood vessel status evaluation device according to claim 7, wherein division of the plurality of scoring segments conforms to a SYNTAX scoring standard.

11. The blood vessel status evaluation device according to claim 7, wherein the blood vessel type of the target patient comprises a first type and a second type, and a distribution of the scoring segments being divided from the target blood vessel pattern in the target image in response to the blood vessel type of the target patient being determined as the first type is different from a distribution of the scoring segments being divided from the target blood vessel pattern in the target image in response to the blood vessel type of the target patient being determined as the second type.

12. The blood vessel status evaluation device according to claim 7, wherein the at least one angiography image comprises a plurality of images from different camera angles, and the operation that the processor analyzes the output of the at least one second deep learning model by the third deep learning model to obtain the blood vessel status of the target patient comprises:

generating a plurality of scoring results corresponding to a target scoring segment; and taking a maximum value corresponding to the target scoring segment in the plurality of scoring results as a final scoring result to describe a blood vessel status of the target scoring segment.

* * * * *